US009896725B2

(12) United States Patent
Lee et al.

(10) Patent No.: US 9,896,725 B2
(45) Date of Patent: *Feb. 20, 2018

(54) REAL-TIME, LABEL-FREE DETECTION OF MACROMOLECULES IN DROPLETS BASED ON ELECTRICAL MEASUREMENTS

(71) Applicant: The Regents of the University of California, Oakland, CA (US)

(72) Inventors: Abraham P. Lee, Irvine, CA (US); Javier Lopez-Prieto, Cambridge, MA (US); Robert Lin, Berkeley, CA (US); Melinda Simon, Irvine, CA (US)

(73) Assignee: The Regents of the University of California Corporation, Oakland, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 14/709,260

(22) Filed: May 11, 2015

(65) Prior Publication Data

US 2015/0322487 A1   Nov. 12, 2015

Related U.S. Application Data

(63) Continuation-in-part of application No. 13/573,750, filed on Oct. 3, 2012, now Pat. No. 9,030,215.

(60) Provisional application No. 61/543,203, filed on Oct. 4, 2011.

(51) Int. Cl.
*C12Q 1/68* (2006.01)
*G01N 27/04* (2006.01)
*G01N 33/487* (2006.01)

(52) U.S. Cl.
CPC ............. *C12Q 1/686* (2013.01); *G01N 27/04* (2013.01); *G01N 33/48707* (2013.01)

(58) Field of Classification Search
None
See application file for complete search history.

(56) References Cited

U.S. PATENT DOCUMENTS

| | | | | |
|---|---|---|---|---|
| 8,613,889 B2* | 12/2013 | Pollack | ............... | B01F 11/0071 422/50 |
| 9,030,215 B2* | 5/2015 | Lee | ........................ | G01R 27/02 324/705 |
| 2008/0003142 A1* | 1/2008 | Link | ..................... | B01F 3/0807 422/82.08 |
| 2012/0021423 A1* | 1/2012 | Colston, Jr. | ........... | B01F 3/0807 435/6.12 |

(Continued)

*Primary Examiner* — Jermele M Hollington

(57) ABSTRACT

A method for detecting presence of a macromolecule of interest in a test droplet. A set of detection electrodes are provided in contact with a fluidic channel. The test droplet is provided in vicinity of the detection electrodes through the fluidic channel. An alternate current (AC) power at a first frequency is applied across the set of detection electrodes. A first measurement value that reflects electrical characteristics (e.g., impedance) of the test droplet at the first frequency is obtained. This value is compared with a corresponding reference value, wherein the corresponding reference value is obtained by measuring a reference droplet containing the macromolecule of interest or free of the macromolecule at the first frequency. The presence of the macromolecule in the test droplet is thus determined based on the comparison.

20 Claims, 9 Drawing Sheets

(56) References Cited

U.S. PATENT DOCUMENTS

| | | | |
|---|---|---|---|
| 2013/0260447 A1* | 10/2013 | Link | G01N 1/38 |
| | | | 435/287.2 |
| 2013/0293246 A1* | 11/2013 | Pollack | B01L 3/502784 |
| | | | 324/671 |
| 2014/0154695 A1* | 6/2014 | Miller | B05B 1/08 |
| | | | 435/6.12 |
| 2015/0330927 A1* | 11/2015 | Lee | G01N 27/023 |
| | | | 435/6.12 |
| 2016/0136643 A1* | 5/2016 | Larson | B01L 3/502715 |
| | | | 506/2 |

* cited by examiner

| | % correct, DNA amplified | % correct, DNA not amplified |
|---|---|---|
| Frequency 1 | 94.7 | 100 |
| Frequency 2 | 94.7 | 100 |
| Frequency 3 | 94.7 | 100 |
| Frequency 4 | 94.7 | 100 |
| Freq 1 + Freq 2 + Freq 4 | 100 | 100 |

REAL-TIME, LABEL-FREE DETECTION OF MACROMOLECULES IN DROPLETS BASED ON ELECTRICAL MEASUREMENTS

CROSS REFERENCE

This patent application is a Continuation-In-Part of co-pending U.S. patent application Ser. No. 13/573,750, filed on Oct. 3, 2012, titled as "REAL-TIME, LABEL-FREE DETECTION OF NUCLEIC ACID AMPLIFICATION IN DROPLETS USING IMPEDANCE SPECTROSCOPY AND SOLID-PHASE SUBSTRATE," which claims the benefit of and priority to U.S. provisional application No. 61/543,203, titled as "REAL-TIME, LABEL-FREE DETECTION OF NUCLEIC ACID AMPLIFICATION IN DROPLETS USING IMPEDANCE SPECTROSCOPY AND SOLID-PHASE SUBSTRATE," filed on Oct. 4, 2011. The foregoing patent applications are herein incorporated by reference in entirety for all purposes.

STATEMENT OF ACKNOWLEDGEMENT

This invention was made with Government Support under Grant No. N66001-10-1-4003, awarded by the Space and Naval Warfare Systems. The Government has certain rights in this invention.

FIELD OF THE INVENTION

The present disclosure is generally related to detection of biological macromolecules. In particular, the disclosure relates to detection of biological macromolecules in suspension within droplets.

BACKGROUND OF THE INVENTION

Polymerase Chain Reaction (PCR) has been widely used to amplify a specific region of a DNA or RNA strand across several orders of magnitude, generating thousands to millions of copies of a particular DNA or RNA sequence. It has long been adopted as a standard procedure in the detection of nucleic acid targets due to the technique's sensitivity and accuracy. Droplet microfluidics' ability to rapidly generate isolated reaction chambers serves as a convenient platform for the adaption of PCR. Because of the synergy, droplet PCR or digital PCR has garnered much research interest in recent years. Real-time PCR is a tool for DNA or RNA quantification that measures the accumulation of DNA or RNA product after each round of PCR amplification.

Conventionally, as a polymerase enzyme completes the complementary strand, a fluorescent label is released from a fluorescent probe, creating a fluorescent signal that is detectable optically. However, the need for fluorescent illumination as well as detection and the processing required to prepare fluorescent markers generally increases the cost of such systems.

SUMMARY OF THE INVENTION

There is a need to reduce the cost of detecting nucleic acid target as well as other types of macromolecules in droplet microfluidics. It would be advantageous to provide a method of PCR detection without the need for fluorescently labeled substrate. It would also be advantageous to provide a detection mechanism feasible for real time detection of biological macromolecules of interest in a high-throughput integrated microfluidic platform.

Accordingly, embodiments of the present disclosure employ a method to verify the completion of a reaction (which is expected to produce macromolecules of interest) by measuring electrical characteristics of test droplets, e.g., electrical impedance, advantageously eliminating the need for fluorescently labeled substrate.

In one embodiment of the present disclosure, a method for detecting presence of a biological macromolecule of interest in a test droplet includes providing a set of detection electrodes in a fluidic channel, providing the test droplet in vicinity of the electrodes, applying an AC power across the electrodes at a first frequency, obtaining a first measurement value reflecting certain electrical characteristics of the test droplet, comparing the measurement value with a corresponding reference value and determining presence of the macromolecules of interest in the test droplet based on the comparison. The corresponding reference value is obtained by measuring a reference droplet containing the macromolecule at the first frequency. The electrical characteristics may be electrical impedance. The macromolecule of interest may be protein, nucleic acid, or etc.

In one embodiment of the present disclosure, the first measurement value is obtained by using an impedance scope in combination with a current amplifier. In one embodiment, the first measurement value and reference value are peak-to-peak voltages derived from respective real time voltage-time plots in respective measuring periods. In one embodiment of the present disclosure, obtaining the first measurement value comprises a differential impedance measurement in a multi-frequency interrogation.

In one embodiment of the present disclosure, a system for detecting presence of a macromolecule of interest in a series of droplets comprises a fluidic channel, a set of detection electrodes in contact with the fluidic channel, an AC power supply operable to apply electrical power across the set of electrodes at a plurality of known frequencies, an electrical measurement device operable to measure certain electrical characteristics of each of the series of test droplets and a processor operable to compare the measured values of the electrical characteristics of the test droplets with corresponding reference value(s), and a processor operable to compare measured electrical characteristics of each of the series of test droplets with a corresponding reference value. A corresponding reference values is obtained by measuring a reference droplet at multiple known frequencies respectively. The corresponding reference droplet is of substantially the same size as the testing droplet and contains the macromolecule of interest.

In one embodiment of the present disclosure, a method for detecting presence of a macromolecule of interest in a test droplet comprising: providing a set of detection electrodes within a fluidic channel, providing the test droplet in vicinity of electrodes, applying high frequency powers across the set of detection electrodes at four different frequencies, measuring electrical impedances of the test droplet at the four frequencies by differential impedance measurements, comparing the measured electrical impedances with corresponding reference electrical impedances obtained by measuring a reference droplet at the four different frequencies respectively. The reference droplet is of substantially the same size as the testing droplet and contains the macromolecules, and determining the presence of the macromolecule in the test droplet based on the comparison. The four high frequency powers may range from 100 Hz to 50 MHz. The four different frequencies may be applied to a set of electrodes in sequence, or simultaneously, or any combination in which four frequencies may be applied to one or more sets of electrodes.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present disclosure is illustrated by way of example, and not by way of limitation, in the accompanying drawings and in which like reference numerals refer to similar elements.

FIG. 6 lists sample detection accuracy results achieved by one frequency interrogation and multiple frequency interrogation respectively in accordance with embodiments of the present disclosure.

DETAILED DESCRIPTION OF THE INVENTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, and components have not been described in detail as not to unnecessarily obscure aspects of the embodiments of the present invention.

Figure 1:
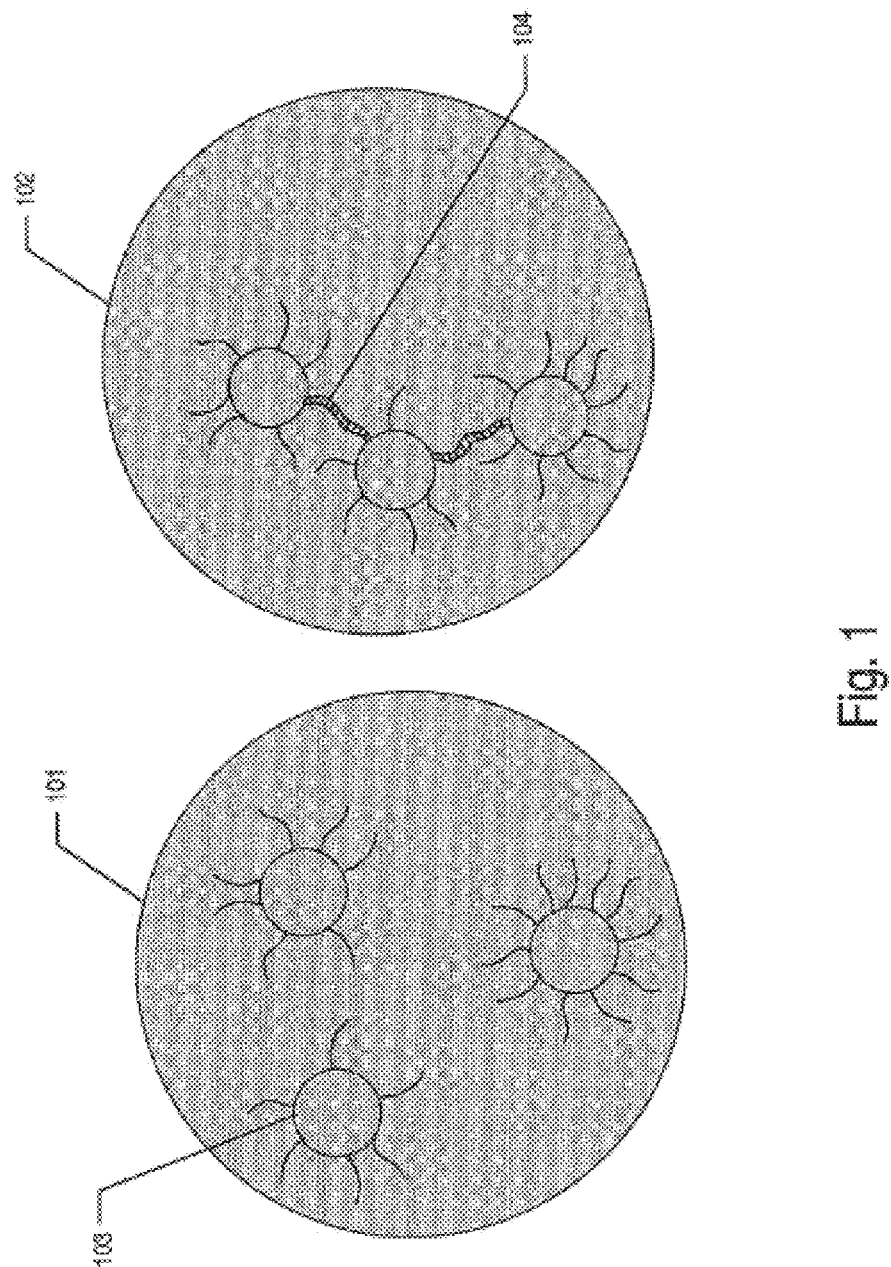
FIG. 1 illustrates the underlying mechanism causing different electrical impedances in a droplet containing non-amplified DNA and a droplet containing amplified DNA, in which detection is aided by the aggregation of solid-phase particles, induced by the amplification of nucleic acid in the droplets.

Real-Time, Label-Free Detection of Macromolecules in Droplets Based on Electrical Measurements Generally speaking, droplets containing amplified DNA or RNA, proteins, enzymes, or other macromolecules may present different electrical characteristics from droplets without the specific macromolecules. The underlying mechanism is illustrated in FIG. 1. When a target DNA or RNA strand is not present in a droplet sample 101, metal nanoparticles or other solid-phase substrates 103 do not aggregate during thermocycling in a polymerase chain reaction (PCR) process. In contrast, with the presence of target DNA or RNA strand 104, primers 104 conjugated to nanoparticles or solid-phase substrates 103 cause aggregation of the nanoparticles or solid-phase substrates 103 in the PCR process. Thereby the electrical impedance of the droplet is changed due to the introduction of the target DNA or RNA strand, which can be measured as the droplet 102 is subject to a certain electrical field in a microfluidic channel. The measurement results, in turn, can be used to determine the presence of amplified DNA or RNA in the droplet.

Nanoparticles or other solid-phase substrates can also be used to enhance the capability for impedance detection of reactions or processes involving proteins, enzymes, or other biological macromolecules. For example, nanoparticles functionalized with biotin will aggregate in the presence of a certain solution concentration of avidin molecules, and the presence or absence of this aggregation will affect the electrical impedance signal obtained, enabling detection of the avidin concentration in the droplet. This approach can also be utilized in other protein detection systems, such as antibody-antigen reactions and immunoassays.

The mechanisms disclosed herein can also be used for Single-Nucleotide Polymorphism (SNP) detection. The solution contains a SNP reaction with an amplified DNA product that is specific for one of the two possible SNPs occurring at one locus for a given sample. The way the assay is designed, the difference between an assay when the primer pairs has a perfect match to the target sequence and thus PCR amplification occurs (wild type) and an assay in which amplification fails (mutant or sequence mismatch resulting from a SNP) can be discriminated by the difference in electric impedance signals.

Figure 2A:
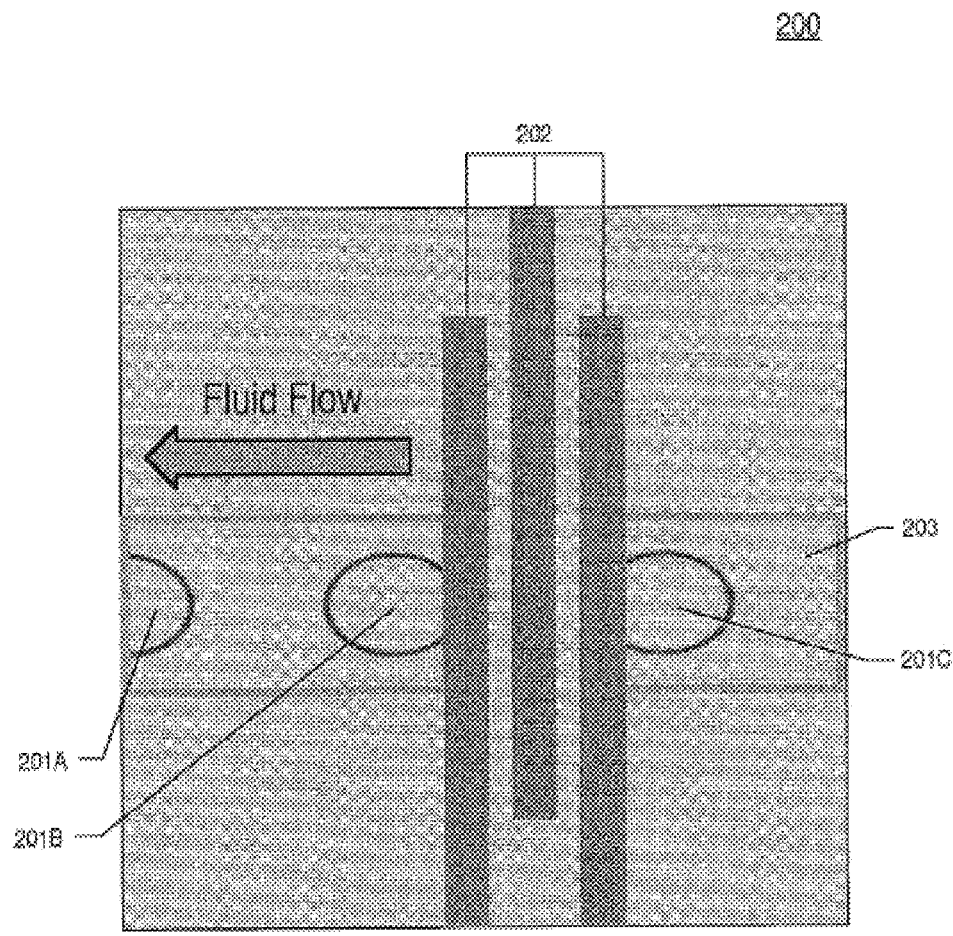
FIG. 2A illustrates a partial configuration of a microfluidic device 200 implementing impedance spectroscopy on the droplets to detect presence of amplified DNA in the droplets in accordance with an embodiment of the present disclosure.

Referring to FIG. 2A. FIG. 2A illustrates a configuration of a microfluidic device 200 implementing impedance measurement on the droplets to detect presence of amplified DNA in the droplets in accordance with an embodiment of the present disclosure. The microfluidic device 200 comprises a microfluidic channel 203 and a set of detection electrodes 202 that are connected to a high frequency or radio frequency power supply for imposing an electrical field on the droplets 201A-201C flowing by. The detection electrodes 202 are spaced and disposed perpendicular to the fluid flow direction in this embodiment. The electrodes may be arranged in either a coplanar (as shown) or parallel configuration (not shown) for these types of measurements. In this embodiment, the set of electrodes 202 consists of 3 gold electrodes.

The present disclosure is not limited to any specific material or configuration of the electrodes used to measure electrical characteristics of test droplets. An electrode may include any sufficiently conducting material. Examples include thin metal films (such as Au, Cr, Pt or ITO), or non-metal conducting material (such as carbon black), etc. An electrode may include non-conductive material coated with conductive material. Conductive thin film in an electrode may feature roughened surfaces to enhance detection. Additionally, multiple sets of electrodes could be used to measure a droplet or set of droplets over time. For example, this could be used to monitor the progress of a nucleic acid amplification or another reaction.

In some embodiments, the test droplet may be measured while it is moving past the detection. In some other embodiments, the measurement may be performed when the test droplet remains stationary.

Figure 2B:
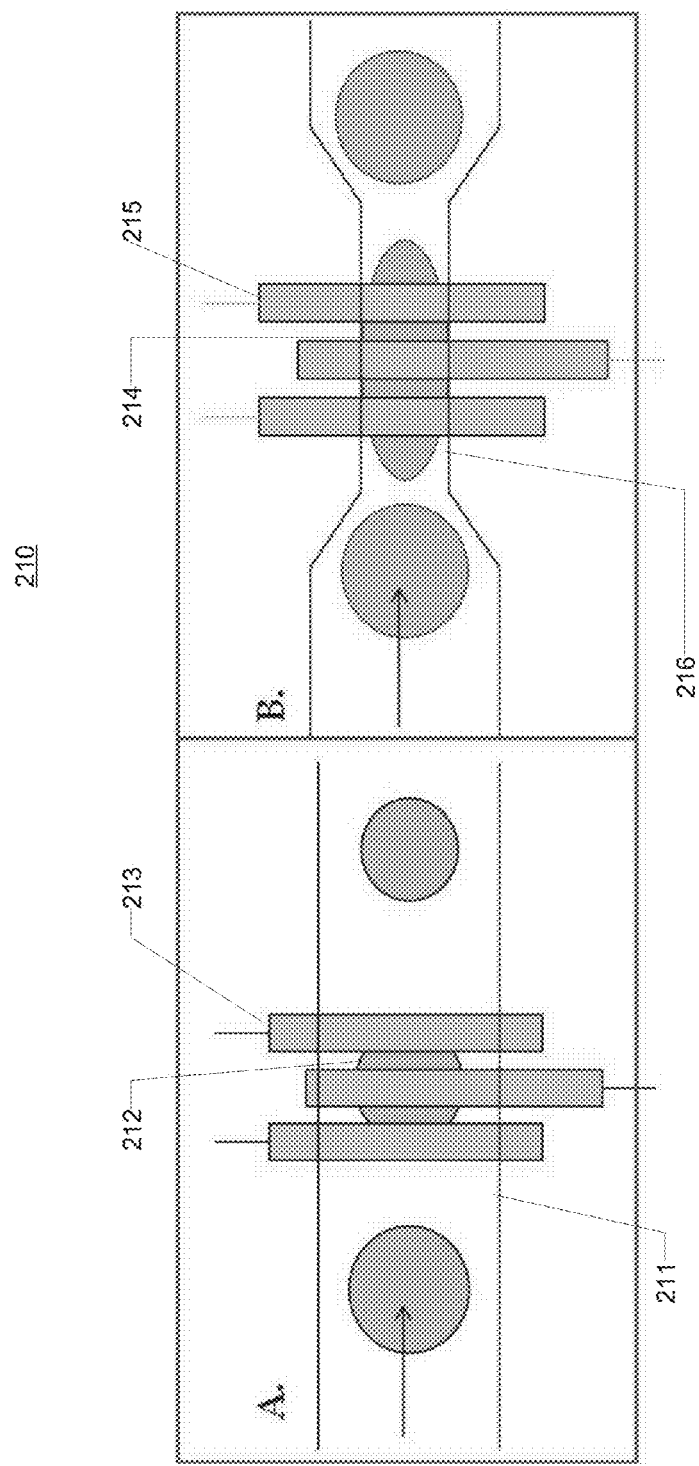
FIG. 2B illustrates the effect of a constriction scheme in a microfluidic channel configuration in accordance with an embodiment of the present disclosure.

In order to enhance the signal-to-noise ratio in detection, the test droplet can be constricted or squeezed as they move over the detection electrodes. In some embodiments, the constriction mechanism is achieved by employing constriction region in the geometry of the microfluidic channel. FIG. 2B illustrates the effect of such a constriction scheme in a microfluidic configuration in accordance with embodiments of the present disclosure. Part A shows a uniform channel geometry 211. When a test droplet 212 is passing the detection electrodes 213 and being measured, its spherical shape is preserved. In contrast, Part B shows a channel with a constricting region 216 over the detection electrodes 215. When a test droplet 214 is passing the constricting region 216 and being measured, it adopts a plug-like conformation. In this configuration, the presence of an oil layer in the channel is minimized, compared to the geometry in Part A, and thereby enabling higher signal-to-noise ratios in detection to be achieved. This constriction mechanism may also enhance the sensitivity and capabilities of an automated detection platform. Other methods or geometries may be used to temporarily displace or drain non-conducting, immiscible phase/fluid surrounding the droplet under measurement.

In some embodiments, differential impedance measurements are employed to determine the electrical impedance of each test droplet, in which an electrical field of a certain frequency is applied to a first two electrodes and then to a second two electrodes. In some embodiments, a common electrode may be shared in the two measurements. The measurements, including excitation signal generation, amplification and demodulation, may be achieved by utilizing an impedance spectroscope (not shown) in combination with a current amplifier (not shown), such as model HF2IS and HF2TA manufactured by Zurich Instruments.

Figure 3A:
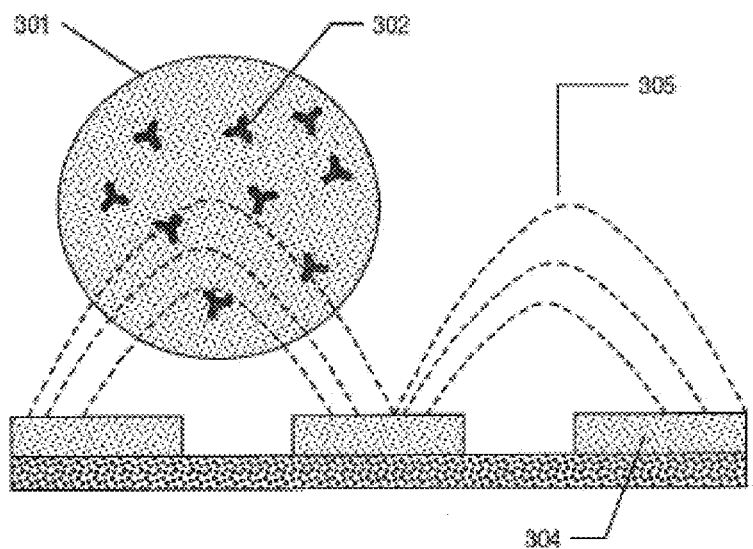
FIG. 3A illustrates a droplet containing unpolymerized DNA monomers flowing over the detection electrodes in accordance with an embodiment of the present disclosure.
Figure 3B:
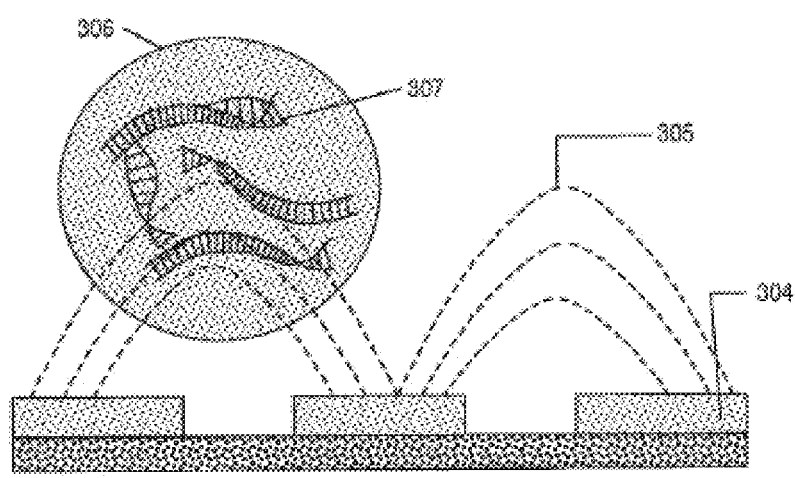
FIG. 3B illustrates a droplet containing polymerized DNA monomers flowing over the detection electrodes in accordance with an embodiment of the present disclosure.

FIG. 3A illustrates a schematic view of a droplet 301 containing unpolymerized DNA monomers 302 flowing over the detection electrodes 304 in accordance with an embodiment of the present disclosure. The dotted lines 305 illustrate electrical field equipotential lines. Also illustrated therein is an exploded view of a single droplet 301 containing unpolymerized DNA monomers 302. By comparison, FIG. 3B illustrates a droplet containing polymerized DNA monomers 307 flowing over the detection electrodes 304 in accordance with an embodiment of the present disclosure. An exploded view of a single droplet 306 containing polymerized DNA monomers 307 is illustrated as well.

Figure 3C:
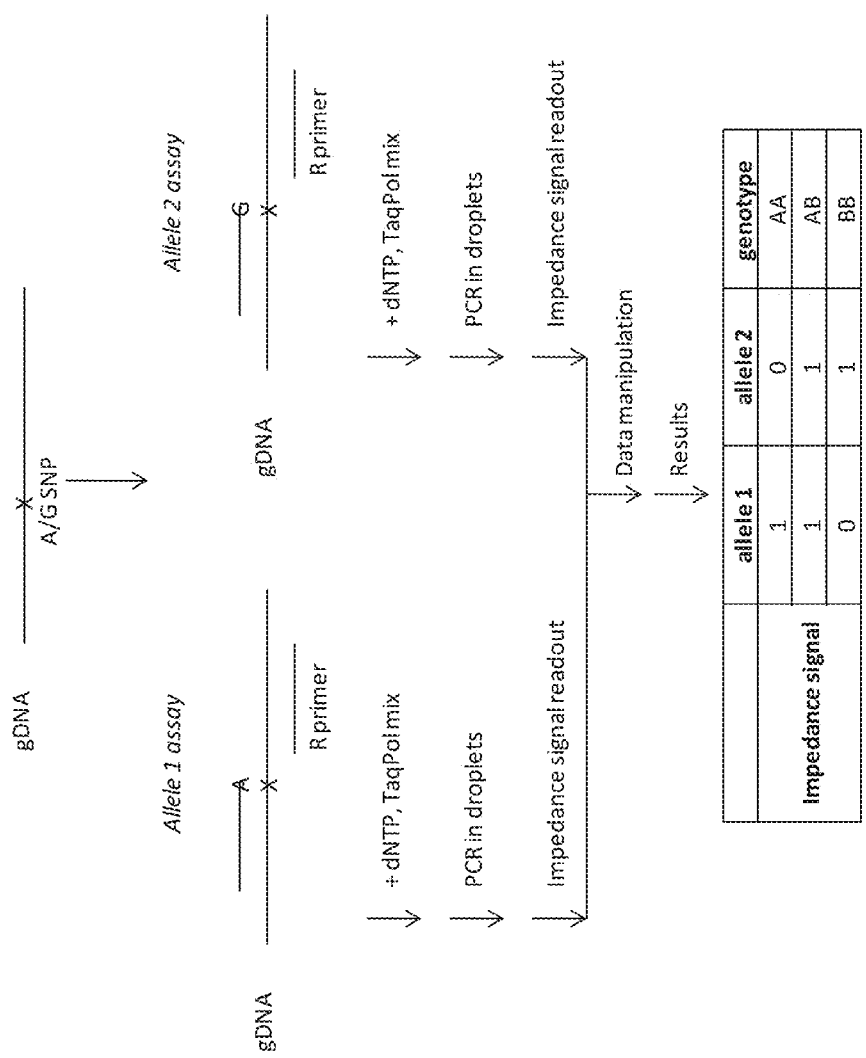
FIG. 3C illustrates a process of using electrical impedance signals for digital SNP discrimination assay in droplets in accordance with an embodiment of the present disclosure.

The mechanism disclosure herein can also be used for SNP detection. FIG. 3C illustrates a process of using electrical impedance signals for digital SNP discrimination assay in droplets in accordance with an embodiment of the present disclosure. The solution contains a SNP reaction with an amplified DNA product that is specific for one of the two possible SNPs occurring at one locus for a given sample. The way the assay is designed, the difference between an assay when the primer pairs has a perfect match to the target sequence and thus PCR amplification occurs (wild type) and an assay failed the amplification (mutant or sequence mismatch resulting from a SNP) can be discriminated by the difference in electric impendence signals.

Figure 4:
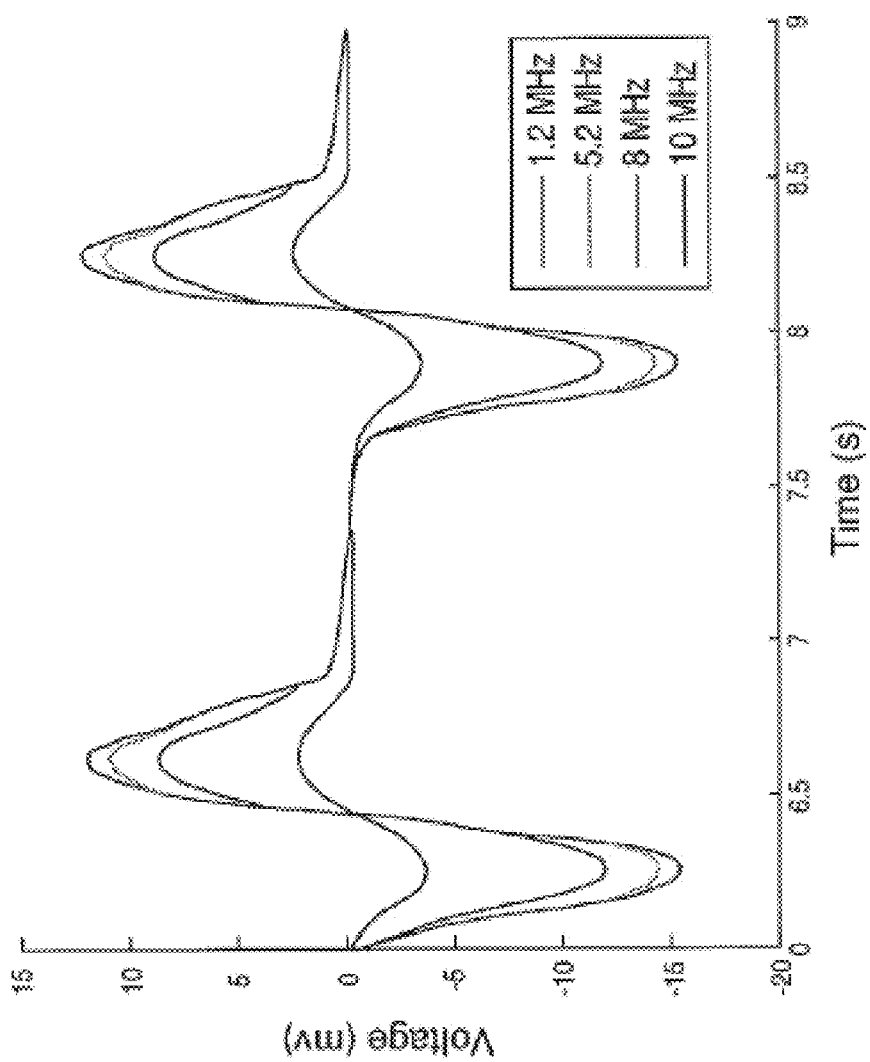
FIG. 4 shows sample voltage-time plots obtained from four-frequency measurement on two consecutive droplets in accordance with an embodiment of the present disclosure.

Referring to FIG. 4. When performing an impedance measurement at a certain excitation frequency on an individual droplet, the impedance spectroscope can produce a real time voltage~time plot. The amplitude of peak-to-peak voltage extracted from the real time plots reflects electrical impedance of the droplet. The peak-to-peak voltage obtained on the test droplet can then be compared with reference electrical impedance value. In some embodiments, the reference electrical impedance values are peak-to-peak voltages obtained from measuring reference droplets known to contain amplified DNA or non-amplified DNA respectively in a similar measuring context with the test droplet measurement, such as the size of the droplets, the frequency applied to the detection electrodes and the conditions of microfluidic channel. In some embodiments, the reference impedance value for a droplet containing non-amplified DNA is obtained by measuring a reference droplet that has not been subject to a PCR procedure. Thus, the presence of amplified DNA on the test droplet is determined based on the comparison.

With respect to detection of a macromolecule of interest in a test droplet by comparing its electrical characteristics with that of a reference droplet, the present disclosure is not limited to specific composition of the reference droplet. For example, a reference droplet may be designed such that it does not contain the macromolecule in sufficient concentration to induce aggregation with nanoparticles/solid phase substrates. Alternatively, a reference droplet is designed such that it includes the macromolecule of interest at a sufficient concentration but without the nanoparticles/solid phase substrates necessary to induce the aggregation. It will be appreciated that the process of comparing electrical characteristics between a test droplet and a reference droplet vary with the composition of the reference droplet.

In some embodiments, the dependency of the amplitude of the peak-to-peak voltage or impedance signal on droplet size and velocity may be removed by taking into account the residence time of the droplet over the measurement electrodes. Using the residence time to normalize these measurements allows for assessment of the contents of the droplets using their electrical impedance measurements, regardless of variations in size or speed that may occur during testing and measurement operations.

Figure 5:
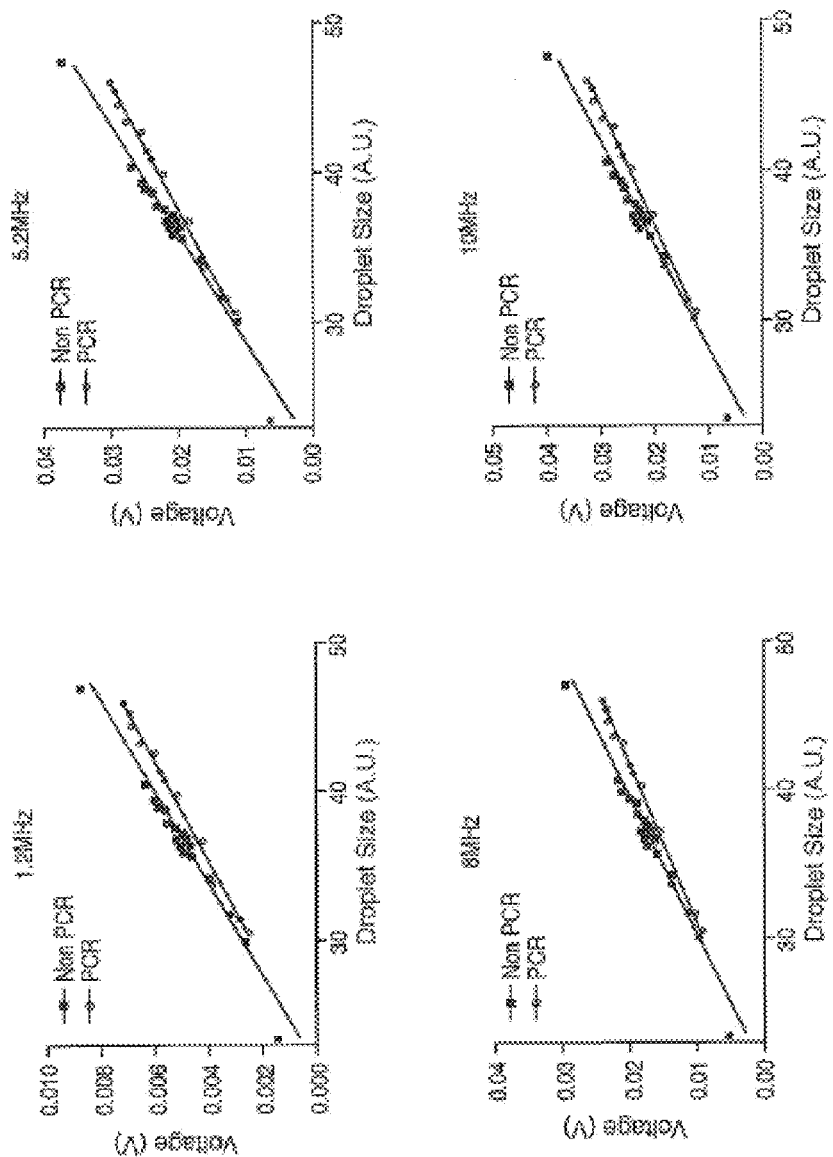
FIG. 5 are sample reference plots of peak-to-peak voltages obtained from measuring reference droplets of a variety of sizes at four frequencies in accordance with an embodiment of the present disclosure.

In some embodiments, a multiple-frequency interrogation scheme and subsequent demodulation can be performed on a single test droplet to determine the presence of amplified DNA for enhanced accuracy. FIG. 4 is sample voltage~time plots obtained from four-frequency measurement on two consecutive droplets in accordance with an embodiment of the present disclosure. The four excitation frequencies are 1.2 MHz, 5.2 MHz, 8 MHz and 10 MHz respectively in this exemplary embodiment. In some other embodiments, the frequencies can be within the range of 100 KHz to 50 MHz. FIG. 5 are reference plots of peak-to-peak voltages obtained from measuring reference droplets of a variety of sizes at each of these four frequencies in accordance with an embodiment of the present disclosure. Each data point represents a single droplet. Linear fitting of the collected peak-to-peak voltage data creates reference curves. The curves show obvious differences in the voltage signals obtained from droplets containing amplified DNA and non-amplified DNA. These reference curves can subsequently be used as a predictor for DNA amplification in test droplets. In some other embodiments, measured electrical impedance can be independent of the sizes of the droplets, sparing the requirement for collecting reference values on different sizes of reference droplets.

In some embodiments, analysis of the impedance data may involve using the magnitude of the electrical impedance. In some other embodiments, the analysis uses only certain features of the impedance, i.e., real or imaginary portions of the impedance measurement, or combination of these.

Although embodiments of the present disclosure are described in detail by referring to measuring electrical impedance of test droplets, any other suitable electrical characteristics dependent on the presence of a macromolecule of interest can also be measured, derived and utilized for detection of such molecules, such as capacitance, inductance, etc.

FIG. 6 lists sample detection accuracy results achieved by one frequency interrogation and multiple frequency interrogation respectively in accordance with embodiments of the present disclosure. It shows that combining measurement results obtained from multiple frequencies provides enhanced discriminatory power in detecting droplets containing either amplified or non-amplified DNA in the droplets.

Figure 7:
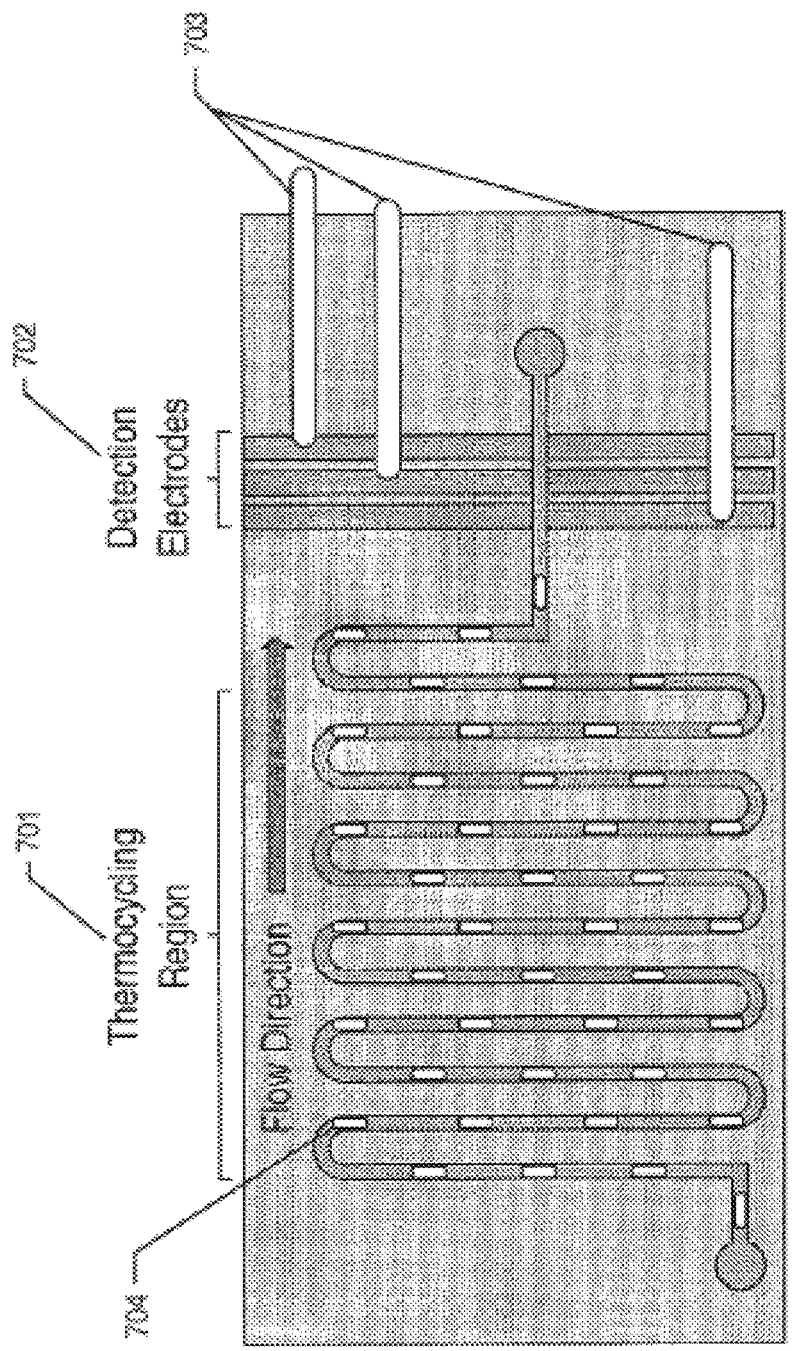
FIG. 7 is a diagram illustrating a droplet-based PCR platform that incorporates impedance-based detection method in accordance with an embodiment of the present disclosure.

FIG. 7 illustrates a schematic view of a droplet based PCR platform that incorporates impedance-based detection method in accordance with an embodiment of the present disclosure. The platform comprises a thermocycling region 701 for the PCR process, a set of detection electrodes 702 and electrical contact pads 703. Test droplets 704 coming from the thermocycling region 701 flow over the detection electrodes 702 through a fluidic channel 704 in sequence. The detection electrodes are coupled with a current amplifier and an impedance spectroscope which provide measurement mechanism for electrical impedance of each droplet in the fluidic channel 704. In some embodiments, the measurement data can be input to a computing device equipped with suitable hardware and software programs substantially in real-time and are processed in a manner compatible with an embodiment of present disclosure. In some embodiments, the platform is made part of an automated system and thereby made suitable for performing label-free DNA detection at high efficiency.

Droplets may be aqueous in nature and surrounded by a continuous phase of oil, or may be lipophilic in nature and surrounded by an immiscible hydrophilic phase. In addition, the droplets may consist of multiple layers (i.e. liposomes or multiple emulsions). For example, a multiple-emulsion droplet may include an aqueous inner phase, surrounded by a hydrophobic layer or lipid-based membrane, and surrounded by a continuous aqueous or hydrophilic phase (i.e. a W/O/W, or water/oil/water multiple emulsion). Liposomes offer the ability to more closely mimic the functions of a biological cell, and the impedance measurement system described here is envisioned as a way to monitor reactions or processes within these cell analogues. The immiscible fluid can be hydrophilic or hydrophobic, depending on the composition of the emulsion droplet.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for detecting presence of a macromolecule of interest in a test droplet, the method comprising:
   providing a set of detection electrodes in contact with a fluidic channel comprising the test droplet;
   providing the test droplet in vicinity of the set of detection electrodes through the fluidic channel;
   applying an alternating current (AC) power at a first frequency across the set of detection electrodes;
   obtaining a first measurement value of the electrical characteristics of the test droplet at the first frequency;
   comparing the first measurement value of the electrical characteristics of the test droplet with a first corresponding reference value; and
   determining presence of the macromolecule of interest in suspension within the test droplet based on the comparison.

2. The method as described in claim 1, wherein the first corresponding reference value is obtained by measuring the electrical characteristics of a reference droplet at the first frequency.

3. The method as described in claim 2, wherein the macromolecule of interest is a protein, and wherein further the reference droplet contains the protein.

4. The method as described in claim 1, wherein the test droplet further comprises a substrate particle, and wherein the macromolecule of interest is conjugated with the substrate particle in the test droplet, and wherein further the substrate particle is solid-phase particle or a nanoparticles.

5. The method as described in claim 1, wherein each of the set of detection electrodes comprises a conductive film coated on a non-conductive material.

6. The method as described in claim 2, wherein both the first measurement value and the first corresponding reference value are peak-to-peak voltages in respective measuring periods and derived by utilizing an impedance scope in combination with an current amplifier.

7. The method as described in claim 2,
   wherein the set of detection electrodes comprise two groups of electrodes wherein the two groups share a common excitation or detection electrode; and
   wherein obtaining the first measurement value further comprises obtaining a differential impedance measurement conducted across the two groups of electrodes respectively.

8. The method as described in claim 7, further comprising:
   performing at least three additional differential impedance measurements on the test droplet at three additional frequencies conducted across the set of detection electrodes;
   comparing peak-to-peak voltage values obtained from the three additional measurements with three corresponding reference values respectively, wherein the three corresponding reference values are obtained by measuring the reference droplet at the three additional frequencies respectively; and incorporating results from the three additional measurements to determine the presence of the macromolecule of interest in the test droplet.

9. The method as described in claim 1 further comprising using additional sets of electrodes in contact with the fluidic channel to monitor the electrical characteristics of the test droplet as a function of time.

10. The method as described in claim 1, wherein the fluidic channel comprises immiscible fluid surrounding the test droplet, and further comprising temporarily displacing the immiscible fluid from the test droplet for obtaining the first measurement value.

11. The method as described in claim 10, wherein the test droplet comprises multiple emulsions, and wherein the immiscible fluid is hydrophilic.

12. The method as described in claim 1 further comprising normalizing the first measurement value with respect to a residence time of the test droplet over the set of detection electrodes such that the first measurement value is independent of size and velocity of the test droplet.

13. A system for detecting presence of a macromolecule of interest in a series of droplets, the system comprising:
a fluidic channel providing a plurality of test droplets;
a set of detection electrodes disposed in contact with the fluidic channel;
an AC power supply operable to apply electrical powers across the set of detection electrodes at a plurality of known frequencies;
an electrical measurement device for measuring an electrical characteristics of the series of test droplets; and
a processor configured to compare a measured value of the electrical characteristics of a respective test droplet of the series of test droplets with a corresponding reference value and to determine presence of the macromolecule of interest in suspension within the respective test droplet based on comparison.

14. The system as described in claim 13, wherein the electrical characteristics is electrical impedance, and wherein further the corresponding reference value is obtained by measuring electrical impedance of a reference droplet at the plurality of known frequencies respectively.

15. The system as described in claim 14, wherein the reference droplet is of substantially the same size as the testing droplets and contains a low concentration of the macromolecule of interest, and wherein the low concentration is insufficient for inducing conjugation of the macromolecule of interest with substrate particles in the reference droplet.

16. The system described as in claim 13, wherein the macromolecule of interest is conjugated with substrate particles in the test droplet, and wherein further the substrate particles are solid-phase particle or nanoparticles.

17. The system as described in claim 13, wherein the macromolecule of interest is an enzyme.

18. The system described as in claim 13 further comprising a thermocycling region for implementing Polymerase Chain Reaction (PCR) on the plurality of test droplets.

19. The system described as in claim 14, wherein the set of detection electrodes comprise two groups of electrodes wherein the two groups share a common excitation or detection electrode; and
wherein the measured value is obtained from a differential impedance measurement conducted across the two groups of electrodes respectively.

20. The system described as in claim 13, wherein the processor is further configured to normalize the measured value with respect to a residence time of the test droplet over the set of detection electrodes such that the measured value is independent of size and velocity of the test droplet.

* * * * *